United States Patent [19]

Carli et al.

[11] Patent Number: 5,164,380
[45] Date of Patent: Nov. 17, 1992

[54] PROCESS FOR PREPARING PIROXICAM/CYCLODEXTRIN COMPLEXES, THE PRODUCTS OBTAINED AND THEIR PHARMACEUTICAL COMPOSITIONS

[75] Inventors: Fabio Carli, Trieste; Paolo Chiesi, Fontanini di Vigatto, both of Italy

[73] Assignee: Chiesi Farmaceutici S.p.A., Parma, Italy

[21] Appl. No.: 676,070

[22] Filed: Mar. 27, 1991

[30] Foreign Application Priority Data

Mar. 27, 1990 [IT] Italy .................. 19829 A/90

[51] Int. Cl.[5] ............ A61K 9/18; A61K 9/20; A61K 47/02; A61K 47/30
[52] U.S. Cl. .................... 514/58; 536/103; 514/226.5; 514/772.3; 514/778; 514/770; 514/499; 514/501; 514/964; 514/965; 424/464; 424/465; 424/468; 424/469; 424/470; 424/489
[58] Field of Search ........... 514/226.5, 58, 772.3, 514/778, 770; 536/103; 424/464, 465, 468, 469, 470, 489

[56] References Cited

U.S. PATENT DOCUMENTS

| | | | |
|---|---|---|---|
| 4,564,614 | 1/1986 | Crawford et al. | 514/226.5 |
| 4,565,807 | 1/1986 | Uekama et al. | 514/58 |
| 4,603,123 | 7/1986 | Chiesi et al. | 514/58 |
| 4,636,343 | 1/1987 | Shibanai | 514/58 |
| 4,672,061 | 6/1987 | Crawford et al. | 514/226.5 |
| 4,824,841 | 4/1989 | Chiesi et al. | 514/226.5 |
| 4,888,343 | 12/1989 | Jones et al. | 514/264 |
| 4,942,167 | 7/1990 | Chiesi et al. | 514/226.5 |
| 5,068,226 | 11/1991 | Weinshenker et al. | 514/58 |
| 5,070,081 | 12/1991 | Majid et al. | 514/58 |

FOREIGN PATENT DOCUMENTS 0153998  9/1985  European Pat. Off.
0371431  6/1990  European Pat. Off.

OTHER PUBLICATIONS

Szejtli, Cyclodextrin Technology, pp. 279–281 (1988).
Duchene et al, Acta Pharmaceutica Technol., vol. 36, No. 1, pp. 1–6 (1990).

Primary Examiner—Ronald W. Griffin
Attorney, Agent, or Firm—Birch, Stewart, Kolasch & Birch

[57] ABSTRACT

A process for preparing complexes of piroxicam with cyclodextrins in which the two components in the powder state are premixed and then co-ground in a high energy mill in the presence of steam.

The products obtained have technological, physical and biopharmacological characteristics which are advantageous compared with those of liquid-state complexes obtained by traditional methods, and are suitable for preparing pharmaceutical compositions for oral, rectal and topical use.

10 Claims, No Drawings

PROCESS FOR PREPARING PIROXICAM/CYCLODEXTRIN COMPLEXES, THE PRODUCTS OBTAINED AND THEIR PHARMACEUTICAL COMPOSITIONS

Piroxicam is a non-steroidal anti-inflammatory drug with considerable analgesic and anti-inflammatory activity.

It is poorly soluble in water and in biological fluids at physiological pH values. Piroxicam is characterised by a slow and gradual absorption via both the oral and rectal routes and this involves a delayed onset of anti-inflammatory and analgesic effect.

The aforegoing underlines the interesting method to ameliorate biopharmaceutical properties is based on including the drug in cyclodextrins, water-soluble natural glycosidic cyclic compounds.

Italian patent 1,196,033 filed on Feb. 22, 1984 describes inclusion complexes of piroxicam and cyclodextrins in a molar ratio between 1:1 and 1:10, preferably 1:2.5. This complex results in much higher solubility than piroxicam alone, improved pharmacokinetic characteristics and improved gastric tolerability.

The processes described in said patent for preparing inclusion complexes of piroxicam in cyclodextrins are all based on the liquid state, comprising dissolving the two components (piroxicam and cyclodextrin) in a suitable solvent and then separating the complexes obtained in the solid state by drying, crystallization, freeze-drying or air-flow atomization (spray-drying).

SUMMARY OF THE INVENTION

A new process has now been found for preparing piroxicam-cyclodextrin complexes characterised in that:
  a) piroxicam and cyclodextrin both in powder form are mixed together in the solid state and optionally degassed;
  b) the mixture obtained is co-ground in a high energy mill whose grinding chamber is saturated with steam;
  c) the product obtained is dried under vacuum and screened to eliminate any aggregates.

The product obtained is a piroxicam/cyclodextrin complex of high density and large surface area which, combined with its extremely fine particle size, make it particularly advantageous in the preparation of pharmaceutical compositions for oral, rectal and topical administration.

DETAILED DESCRIPTION OF THE INVENTION

The characteristics and advantages of the process for preparing piroxicam-cyclodextrin complexes, the product obtained and the relative pharmaceutical compositions according to the present invention will be more apparent from the following detailed description.

Said process is based on dry preparation. In a first stage the piroxicam and cyclodextrin both in the finely divided powder state are mixed together in a powder mixer, the mixture optionally being degassed under vacuum at room temperature or with slight heating.

In a second stage the mixture of piroxicam and cyclodextrin is co-ground in a high energy mill with the grinding chamber saturated with steam.

In a third stage the product obtained is dried under vacuum at room temperature or with slight heating and sieved to eliminate any aggregates. The piroxicam and cyclodextrin used in the process have a particle size less than 60 mesh and are fed to the mill in a weight ratio of cyclodextrin to piroxicam between 10:1 and 1:1.

The co-grinding is conducted for a time of between 0.10 and 48 hours and preferably for a time between 0.25 and 4 hours.

The product obtained is screened through a 60 mesh screen and homogenized by mixing.

The product is characterized by a high density, a large surface area and an extremely fine particle size, good solubility and a low water contact angle.

It consists of a piroxicam/cyclodextrin molecular inclusion complex, as demonstrated by IR spectrophotometry and DSC (differential scanning calorimetry) analysis.

Because of its characteristics, the piroxicam/cyclodextrin complex according to the invention can be advantageously used to prepare pharmaceutical compositions having analgesic, anti-inflammatory and antirheumatic activity, for oral, rectal and topical administration.

For example, tablets prepared with the complex of the present invention have a much higher dissolution rate than commercial formulations containing piroxicam alone.

"In vivo" trials have shown that the complexes of the invention provide more rapid absorption than commercial formulations of uncomplexed piroxicam.

Compositions for oral or rectal administration contain between 10 and 50 mg of said complex per unit dose, while compositions for topical administration contain between 0.2 and 5% by weight of said complex.

Using the complex of the present invention, tablets of rapid disintegration and high dissolution rate can be specifically prepared in which the content of the piroxicam-cyclodextrin complex is between 40 and 60% by weight, with colloidal silica, lactose, crospovidone, magnesium stearate and optionally starch and carboxymethylstarch as excipients.

Finally, in addition to the aforesaid advantages it must be emphasized that the process according to the invention results in considerable cost and industrial advantages due to the simplicity of the operations and equipment.

The following examples relating to the preparation of piroxicam/cyclodextrin complexes, their characterisation, their pharmaceutical compositions and their in vivo application better illustrate the invention.

EXAMPLE 1

4 grams of piroxicam and 12 grams of betacyclodextrin are screened through a 60 mesh screen and mixed for 10 minutes in a suitable mixer. The mixture is fed into the co-mixing chamber of a roto-centrifugal high energy mill together with the grinding means in a weight ratio of 1:5.5.

The grinding chamber is saturated with steam by opening a connection valve between the chamber and a steam reservoir, and co-grinding is then conducted for two hours. On termination of this operation the product is discharged, screened through a 60 mesh screen and homogenized by mixing.

EXAMPLE 2

200 grams of piroxicam and 1720 grams of betacyclodextrin are screened through a 60 mesh screen and fed into the grinding chamber of a high energy vibration mill together with the grinding means in a weight ratio of 1:2.34.

While maintaining the mill at its minimum vibrational frequency the powders are exposed for 15 minutes to a flow of steam by opening a connection valve between the chamber and a steam reservoir (mixing and activation stage).

After this operation the true co-grinding stage is effected for 4 hours. On termination, the product is discharged, screened through a 60 mesh screen and homogenized by mixing.

Physical and chemical characteristics of the piroxicam(P)-β-cyclodextrin complex (β-CD)

Evidence of P/β-CD interaction in the products of Examples 1 and 2 was demonstrated by IR spectrophotometry and DSC (differential scanning calorimetry).

Table 1 shows the DSC data determined under the following operating conditions: starting temperature 35° C.; final temperature 240° C.; heating rate 10° C./min.

To verify that complexing is complete, the reference value to be taken is the heat of fusion of piroxicam alone at its melting point (202°–203° C.).

TABLE 1

| Piroxicam/β-CD complex | Differential scanning calorimetry (DSC) | |
|---|---|---|
| | Melting point °C. | Heat of fusion J/g |
| Example 1 | 189.0 | 14.2 |
| Example 2 | 192.3 | 7.5 |

Physico-pharmaceutical characterisation of the piroxicam/betacyclodextrin complex Data are given relevant to water-wettability determined by water contact angle analysis, true density determined by Helium pycnometry, and surface area determined by mercury porosimetry (Table 2).

TABLE 2

Physico-pharmaceutical characterisation parameters of various piroxicam/β-CD complexes compared with the starting raw material

| Compound | true density (g/ml) | water contact angle | surface area (m²/g) |
|---|---|---|---|
| piroxicam | | 76° | |
| Freeze-Dried piroxicam/β-CD | 1.51 | 45°50' | 0.30 |
| spray-dried piroxicam/β-CD | 1.29 | 54°79' | 0.85 |
| piroxicam/β-CD of Example 1 | 1.74 | 35°89' | 2.07 |

Solubilization kinetics tests were also conducted on the piroxicam/β-CD complex (500 ml of acetate buffer pH 5.0, 125 rpm, 37° C.), in which a product quantity at least 10 times greater than that required to saturate the solution (oversaturation value) was placed in a dissolution test apparatus (paddle method) equipped with a continuous flow cell allowing continuous spectrophotometric detection of dissolved piroxicam in a very short-time (1 to 5 seconds). This test, effected within a few minutes from the beginning of the solubilization process, provides data to be considered as one of the most important parameters for the biopharmaceutical evaluation of the products.

Comparison of solubility of various piroxicam/β-CD complexes prepared by different methods and uncomplexed product are shown in Table 3.

TABLE 3

Solubility data of different piroxicam/β-CD preparations compared with uncomplexed product.

| Compound | Equilibrium solubility (mg/l) | C max (oversaturation value) (mg/l) |
|---|---|---|
| piroxicam | 30 | 30 |
| freeze-dried piroxicam/β-CD | 81 | 883.2 |
| spray-dried piroxicam/β-CD | 73.1 | 317.9 |
| piroxicam/β-CD of Example 1 | 80.2 | 272.3 |

EXAMPLE 3

The following formulation was used to prepare fast disintegration tablets with high dissolution rate: 30% by weight of co-ground piroxicam-cyclodextrin was premixed with colloidal silica and screened through an 18 mesh screen. After adding the remaining co-ground product mixing was continued for a further 15 minutes.

All the remaining prescreened excipients were added and mixing continued for a further 15 minutes. The mixture was finally formed into tablets.

The unit composition of the tablets obtained in this manner is as follows:

| | |
|---|---|
| Co-ground piroxicam/cyclodextrin | 215 mg |
| Colloidal silica | 10 mg |
| Spray-dried lactose | 87 mg |
| Starch | 10 mg |
| Carboxymethylstarch | 20 mg |
| Crospovidone | 50 mg |
| Magnesium stearate heavy powder | 8 mg |
| Total | 400 mg |

The tablets have a hardness of about 10 kgp and an average disintegration time of 2 min 30 sec. Dissolution rate data are shown in Table 4.

EXAMPLE 4

Even more rapidly disintegrable tablets with an even higher dissolution rate were obtained by the following formulation: all the components including the co-ground piroxicam-cyclodextrin were mixed together, screened through a 40 mesh screen and further mixed for a suitable time period.

The mixture obtained was then formed into tablets. Their unit composition is as follows:

| | |
|---|---|
| Co-ground piroxicam/cyclodextrin | 210.32 mg |
| Colloidal silica | 3 mg |
| Spray-dried lactose | 130.68 mg |
| Crospovidone | 50 mg |
| Magnesium stearate heavy powder | 6 mg |
| Total | 400 mg |

The tablets have an average disintegration time of 1 min 30 sec and a very high dissolution rate, as shown in Table 4.

Dissolution rate of tablets containing the piroxicam/betacyclodextrin complex

The dissolution rate of tablets containing as active ingredient the piroxicam/β-cyclodextrin complex prepared in Example 2 was compared with that of analogous pharmaceutical compositions containing as active ingredient piroxicam/β-cyclodextrin inclusion complex obtained by different methods and with a standard commercial piroxicam composition.

TABLE 4

Dissolution rate of various solid oral compositions of piroxicam standard and of piroxicam/β-cyclodextrin complexes

| Compound | Composition | Mean percentage dissolved at various times | | | | | |
|---|---|---|---|---|---|---|---|
| | | 60 sec | 120 sec | 180 sec | 240 sec | 300 sec | 600 sec |
| piroxicam | capsules | 0.00 | 3.02 | 44.00 | 57.08 | 78.62 | 93.66 |
| Piroxicam/β cyclodextrin complex prepared by spray-drying | tablets | 16.69 | 50.62 | 80.58 | 97.99 | 104.34 | 107.59 |
| Piroxicam/β cyclodextrin complex prepared by freeze-drying | tablets | 9.33 | 24.97 | 42.69 | 59.39 | 74.64 | 101.64 |
| Piroxicam/β cyclodextrin complex prepared in Example 2 | tablets (Example 3) | 22.13 | 67.00 | 93.59 | 97.11 | 98.12 | 98.88 |
| Piroxicam/β cyclodextrin complex prepared in Example 2 | tablets (Example 4) | 31.44 | 85.88 | 100.14 | 101.59 | 101.93 | 102.13 |

As can be seen from the data of Table 4, tablets containing the piroxicam/β-cyclodextrin complex have a dissolution rate which is quite higher than the commercial formulation containing crystalline piroxicam standard. Moreover it is interesting to note that significant differences exist also among piroxicam/β-cyclodextrin complexes. The dissolution profile of the tablets prepared following Example 3 and Example 4 particularly emphasize the importance of the formulation and the optimum choice of excipients.

Pharmacokinetic characterisation

Pharmacokinetic studies were conducted in healthy volunteers to determine the "in vivo" importance of the physico-pharmaceutical characteristics of the pharmaceutical compositions of the invention. Various compositions containing as active ingredient the piroxicam/β-cyclodextrin complex prepared by different methods (freeze-drying, spray-drying and co-grinding) were compared one another and with a standard commercial composition.

The compositions were administered to the volunteers in accordance with standard administration, feeding and wash-out period procedures.

For all pharmaceutical forms the administered dose (single dose) was 20 mg of piroxicam. The plasma concentrations of piroxicam were determined by a validated HPLC analysis method.

The results are shown in Table 5. As can be seen from the data reproduced in this table, significant differences in plasma level were observed during the initial 120 minutes after administering the various compositions.

Besides confirming that the absorption of the complexes is more rapid than that of the commercial uncomplexed piroxicam formulation, these results further emphasize the importance of the pharmaceutical composition itself.

In this respect, the pharmacokinetic characteristics of the complexes reproduce the pattern both of the dissolution rate and the solubilization kinetics.

TABLE 5

Plasma levels and pharmacokinetic parameters of different solid oral compositions of standard piroxicam and of piroxicam/β-cyclodextrin (P/β-Cl) complexes (N = 4; cross-over study)

| Formulation | Plasma level (mcg/ml) (X + SE) at various times | | | | | | | Cmax (mcg/ml) | Tmax (h) | AUC (0–2 h) (mcg/ml) · h | AUC (0–24 h) (mcg/ml) · h |
|---|---|---|---|---|---|---|---|---|---|---|---|
| | 0.25 | 0.50 | 1.0 | 2.0 | 4.0 | 8.0 | 24.0 (h) | | | | |
| piroxicam capsules | 0.31 | 1.37 | 1.44 | 1.48 | 1.26 | 1.37 | 1.02 | 1.65 | 4.60 | 2.41 | 29.10 |
| | ±0.20 | ±0.27 | ±0.23 | ±0.21 | ±0.21 | ±0.32 | ±0.09 | ±0.15 | ±1.90 | ±0.39 | ±4.41 |
| freeze-died P/β-Cl (tablets) | 1.27* | 2.25 | 2.08* | 2.22* | 1.87 | 2.04 | 1.31 | 2.40* | 3.10 | 3.76* | 42.10 |
| | ±0.15 | ±0.18 | ±0.05 | ±0.15 | ±0.14 | ±0.13 | ±0.03 | ±0.08 | ±1.60 | ±0.14 | ±1.10 |
| Spray-dried P/β-Cl (tablets) | 0.92 | 1.39 | 2.16 | 2.31 | 1.84 | 1.84 | 1.25* | 2.36 | 1.50 | 3.52 | 39.78 |
| | ±0.20 | ±0.26 | ±0.23 | ±0.31 | ±0.10 | ±0.17 | ±0.08 | ±0.28 | ±0.30 | ±0.44 | ±3.32 |
| P/β-Cl of Example 4 (tablets) | 1.54* | 2.31 | 1.98 | 2.16* | 1.68 | 1.80 | 1.27 | 2.34* | 0.88 | 3.82* | 39.19 |
| | ±0.11 | ±0.07 | ±0.13 | ±0.12 | ±0.10 | ±0.11 | ±0.04 | ±0.06 | ±0.038 | ±0.17 | ±1.17 |

*p 0.05 vs piroxicam cps
Cmax = maximum plasma concentration
Tmax = time to maximum concentration
AUC = area under the plasma concentration-time curve at 0–2 hours and 0–24 hours from administration.

We claim:

1. A process for preparing piroxicam-cyclodextrin complexes which comprise:
   a) mixing piroxicam and a cyclodextrin together in a solid state to produce a mixture;
   b) co-grinding said mixture in a high energy mill, wherein the grinding chamber is saturated with steam to produce a product.
   c) drying said product under vacuum, and
   d) screening the thus produced dried product to eliminate aggregates.

2. The process as claimed in claim 1, wherein the weight ratio of cyclodextrin to piroxicam is between 10:1 and 1:1.

3. The process as claimed in claim 1, wherein the co-grinding is conducted for a time of between 0.10 and 48 hours.

4. The process as claimed in claim 1, wherein the co-grinding is conducted for a time of between 0.25 and 4 hours.

5. A piroxicam/cyclodextrin complex obtained by the process of claim 1.

6. A pharmaceutical composition with analgesic, anti-inflammatory and antirheumatic activity which comprises as an active ingredient the complex of claim 5, together with a pharmaceutical excipient.

7. The composition as claimed in claim 6 which is suitable for oral or rectal administration containing between 10 and 50 mg of said complex per unit dose.

8. The composition as claimed in claim 6 which is suitable for topical administration containing between 0.2 and 5% by weight of said complex.

9. The composition as claimed in claim 6 in the form a of tablet comprising said piroxicam/cyclodextrin complex in an amount of between 40 and 60% by weight and a pharmaceutically acceptable excipient selected from the group consisting of colloidal silica, lactose, cross linked polyvinylpyrrolidone, magnesium stearate, starch and carboxy-methyl starch.

10. The process according to claim 1, wherein said mixture is degassed.

* * * * *